United States Patent
Haywood et al.

(10) Patent No.: US 9,116,082 B1
(45) Date of Patent: Aug. 25, 2015

(54) DEEP WATER SAMPLER

(76) Inventors: Carl Ray Haywood, Jasper, AL (US);
Lisa Ann Moore Haywood, Jasper, AL (US)

( * ) Notice: Subject to any disclaimer, the term of this patent is extended or adjusted under 35 U.S.C. 154(b) by 307 days.

(21) Appl. No.: 13/482,908

(22) Filed: May 29, 2012

Related U.S. Application Data

(60) Provisional application No. 61/519,472, filed on May 23, 2011.

(51) Int. Cl.
G01N 1/20 (2006.01)

(52) U.S. Cl.
CPC ..................................... G01N 1/2035 (2013.01)

(58) Field of Classification Search
CPC .................. G01N 1/2035; G01N 2001/205
USPC ....................................................... 73/863.86
See application file for complete search history.

(56) References Cited

U.S. PATENT DOCUMENTS

| | | | | |
|---|---|---|---|---|
| 4,756,310 A * | 7/1988 | Bitterly | ........................ | 607/104 |
| 4,809,909 A * | 3/1989 | Kukesh | ............................. | 239/1 |
| 5,562,132 A * | 10/1996 | Siegele et al. | ................. | 141/198 |
| 7,140,405 B2 * | 11/2006 | Lewis et al. | .................... | 141/104 |
| 7,753,290 B2 * | 7/2010 | Jacques et al. | ................ | 239/329 |
| 2006/0108151 A1 * | 5/2006 | Moore et al. | ..................... | 175/99 |
| 2009/0008477 A1 * | 1/2009 | Merchant | ...................... | 239/305 |
| 2010/0170801 A1 * | 7/2010 | Metzger | ........................ | 205/101 |
| 2010/0320027 A1 * | 12/2010 | Chelminski | .................. | 181/120 |
| 2011/0103778 A1 * | 5/2011 | Batts | ............................. | 392/405 |
| 2012/0291627 A1 * | 11/2012 | Tom et al. | ........................... | 95/8 |
| 2012/0318521 A1 * | 12/2012 | Franklin et al. | ............... | 166/363 |
| 2012/0318522 A1 * | 12/2012 | Franklin et al. | ............... | 166/363 |

* cited by examiner

*Primary Examiner* — Hezron E Williams
*Assistant Examiner* — Rodney T Frank
(74) *Attorney, Agent, or Firm* — C. Brandon Browning; Maynard Cooper & Gale

(57) ABSTRACT

The present invention relates to an apparatus and method for sampling, retrieving and storing fluid samples obtained from a liquid environment. An embodiment comprises a sample holding unit, at least one check valve, a trigger valve coupled to a triggering mechanism, and a decanting valve. Alternatively, apparatus comprises a holding unit, a four-way connector, at least one pressure relief device, a first flow regulating valve, a second flow regulating valve, and a ball valve. A method for sampling, retrieving and storing fluid samples obtained from a liquid environment includes deploying a sample apparatus to the site of interest in a liquid environment, opening the trigger valve with the triggering mechanism, allowing fluid to enter the sample holding unit until the internal pressure becomes substantially equivalent to the external pressure, once check valve closes, the triggering mechanism closes the trigger valve and the sample apparatus is retrieved from the liquid environment.

20 Claims, 6 Drawing Sheets

DEEP WATER SAMPLER

This application claims the benefit of filing priority under 35 U.S.C. §119 from provisional patent application Ser. No. 61/519,472 filed May 27, 2011 titled, ERS Deep Water Sampler. All information disclosed in those prior applications is incorporated herein by reference.

TECHNICAL FIELD OF THE INVENTION

This invention relates, in general, to the sampling of fluids from a liquid environment and, in particular to, a sampling apparatus for obtaining fluid samples and maintaining the samples at substantially near-identical to native environmental conditions upon retrieval and holding.

BACKGROUND OF THE INVENTION

Obtaining and maintaining samples in the samples' native state from fluid environments can be difficult because of the environment of the fluid environment. Depending on the depth of interest or the chemistry of the fluid environment, these environments can vary starkly from the surface environment in terms of pressure and temperature. Some fluid environments possess extreme chemical characteristics, such as high acidity, high alkalinity or extreme anoxia. To fully understand and characterize fluids or microorganisms found in these liquid environments, a sampling apparatus must be able to obtain samples under varied environmental conditions, store said samples at substantial similar conditions as the ambient conditions of the retrieval site, and maintain said environmental conditions as sample is transferred from sampling apparatus.

Use of faulty sampling apparatuses unable to maintain the native environmental conditions of the fluid samples causes alterations of the physical and chemical nature of the fluid samples. Changes in temperature and pressure can cause the fluid samples to approach or reach saturation pressure causing gas stripping. Gas stripping occurs when gases and volatiles exsolve with increasing temperature and decreasing pressure. Bubble formation then leads to a loss of these gases. If the ambient conditions of the fluid sample's retrieval site are not maintained, the resultant changes in pressure, temperature or other environmental variants will result in alterations in the sample that render data analysis fruitless.

Berger et al., U.S. Pat. No. 5,806,186 disclose an apparatus and method for obtaining samples of formation fluid using a work string designed for performing other downhole work such as drilling, workover operations or re-entry operations. The apparatus includes sensors for sensing downhole conditions. The apparatus also includes a relatively small integral sample chamber coupled to multiple input and output valves for collecting and housing a formation fluid.

Taylor et al., U.S. Pat. No. 6,561,046, disclose an apparatus that allows multiple uncontaminated samples to be taken from hydrothermal vents and the oceanic or limnological water columns. The apparatus includes a sampling nozzle for taking in the sample and includes at least one sampling module for the collection of a predetermined type of sample. A fluid intake module is in fluid communication with the sample collection unit and the sampling nozzle. The fluid intake module includes at least one pump for drawing a sample through the sampling nozzle and sample collection unit. In operation the sampling nozzle is moved into a desired sampling location and a micro-controller sends a signal to the fluid intake module to initiate collection of a sample.

Armstrong et al., U.S. Pat. No. 4,660,423, disclose an apparatus for taking water samples from wells, streams, lakes or the like wherein the water sample is to be duplicative of the water that is being tested. The apparatus consists of a carrier adapted to be lowered on a line to any depth in to the water body to be sampled. The carrier is hollow and has an internal load carrying cavity in which a unit consisting of an isolation vial filled with distilled water and a sample collection vial which is evacuated and positioned within the isolation vial are loaded. Both vials are equipped with closing plugs therein which contain septums and a hollow needle structure is provided which pierces the isolation vial septum and extends into but does not pierce the sample collecting septum. In response to a jerk on the line, the carrier exerts a force on the needle unit which causes it to pierce the spectrum in the sample vial thereby communicating the interior of the sample vial with the water to be sampled, with the result that a sample of the water to be tested rushes into the sample vial.

SUMMARY OF THE INVENTION

The present invention is directed to a fluid sampling apparatus and a method for obtaining fluid samples from an environment where the fluid samples are not altered physically or chemically during collection, retrieving the fluid samples and holding of the fluid samples. The use of the term "fluid" is to be understood to include liquids and gases. According to one aspect of the invention, there is provided an apparatus for obtaining at least one fluid sample from a liquid environment where the apparatus is in selective fluid communication with the liquid environment. The apparatus is generally composed of a sample holding unit, a plurality of valves and a triggering mechanism that permits or restricts fluid from the liquid environment from the apparatus. The sample holding unit is configured to be selectively in fluid communication with the surrounding liquid environment and is operable to receive the fluid sample therefrom. A check valve is positioned at the inlet of the sample holding unit and a triggering valve is positioned at an end of check valve where trigger valve communicates with the liquid environment. The apparatus is deployed to a site of interest and the trigger valve is opened by a triggering mechanism, thus allowing fluid to flow through the trigger valve and the check valve and enter the sample holding unit. Once the pressure of the interior of the sample holding unit is substantially equivalent to the exterior of the sample holding unit, the check valve automatically closes, preventing fluid from continuing to flow into the sample holding unit. The trigger valve is closed by the triggering mechanism and the sample holding unit is retrieved from the liquid environment.

According to one method of operating the apparatus, the sample holding unit may be pressurized to a pressure that is substantially equivalent to the site of interest prior to deployment and then deployed to the desired depth of the liquid environment with the trigger valve and a decanting valve in the closed position. When the apparatus achieves the depth of interest, the trigger valve is opened by the triggering mechanism allowing the pressurized gas to exit through the trigger valve and fluid to enter the sample holding unit from the inlet check valve. Once the pressure within the interior of the sample holding unit is substantially equivalent to the pressure of the exterior of the sample holding unit, the check valve closes, stopping fluid from continuing to flow into the sample holding unit. The trigger valve is then closed by the triggering mechanism and the sample holding unit is retrieved from the liquid environment.

According to another aspect of the invention, there is provided an apparatus for obtaining at least one fluid sample from a liquid environment, the apparatus including a sample holding unit, at least one four-way connector, at least one pressure relief device, at least one flow regulating valve and a ball valve. The sample holding unit is selectively in fluid communication with the surrounding liquid environment and operable to receive the fluid sample therefrom. The sampling apparatus can be deployed with a Remote Controlled Vehicle ("ROV") allowing a user controlling the ROV to monitor the sampling apparatus. When the sampling apparatus achieves the depth of interest, the ball valve is opened allowing fluid from the fluid environment to flow through the ball valve, at least one of the flow regulating valve and enter the sample holding unit. Once the pressure within the interior of the sample holding unit reaches the desired level, the ball valve closes stopping fluid from flowing into the sample holding unit, and the sampling apparatus is retrieved from the liquid environment. If the pressure in the apparatus becomes too high, the pressure relief device allows pressure to vent from the apparatus.

A separation apparatus may be coupled to the sampling apparatus where the separation apparatus separates components of interest from composite fluids collected from the liquid environment. The separation apparatus includes a separation chamber with a first end coupled to the sampling apparatus and a second end in open fluid communication with a liquid environment. In use, the separation chamber is deployed coupled to the sampling apparatus. The composite fluids enter the interior of the separation chamber and the component of interest is allowed to separate from the composite fluids, accumulating adjacent and below the first opening of the separation chamber, pushing the remaining fluids in the composite fluid vertically away from the first opening of the separation chamber. When the component of interest has substantially separated from the composite fluid, the component of interest is transferred from separation chamber to the sampling apparatus. Separation and transfer of the component of interest can continue until either the sampling apparatus reaches a specific pressure indicating that maximum capacity is reached in sample apparatus or no further component of interest can be separated from the surrounding fluids.

According to another aspect of the invention, there is provided a method for obtaining at least one fluid sample from a liquid environment. The method includes positioning a sampling apparatus at a desired depth for fluid sampling, obtaining and storing a fluid sample in a sample holding unit of the sampling apparatus and retrieving the sample apparatus with the fluid sample where the fluid sample is kept at substantially the same pressure as the pressure at site of collection of the fluid sample. A temperature altering mechanism can be used to maintain the fluid sample at the temperature of the retrieval site.

According to another aspect of the invention, there is provided a sampling apparatus for collecting fluid samples from fluid environments, the apparatus including a sample holding unit having an interior wall and an exterior wall creating an interior holding space, at least one opening allowing the interior holding space to be selectively in fluid communication with the exterior of the sample holding unit and operable to receive at least a portion of the fluid environment; a first check valve having a first end coupled to a first opening of the at least one opening of the sample holding unit wherein the check valve opens in response to a pressure differential between the interior holding space of the sample holding unit and the exterior of the sample holding unit; a trigger valve having a first opening, a second opening and an actuator wherein the first opening of the trigger valve is coupled to a second opening of the check valve and the actuator moves the trigger valve from a closed position preventing fluid from passing into the sample holding unit to an open position allowing fluid to flow through the trigger valve and the first check valve into the interior holding space of the sample holding unit; and a triggering mechanism coupled to the actuator of the trigger valve wherein trigger mechanism operates the actuator of the trigger valve.

The sampling apparatus may include a second check valve having a first opening coupled to a second opening of the at least one opening of the sample holding unit and a second opening; and a decanting valve having a first opening, a second opening and an actuator wherein the first opening is coupled to the second opening of the second check valve and the actuator moves the decanting valve from a closed position preventing fluid in the interior holding space of the sample holding unit to flow out of the sample holding unit to an open position allowing fluid to flow from the sample holding unit through the second check valve and the decanting valve to the exterior of the sample holding unit. The sample holding unit, first check valve, the trigger valve, the second check valve and the decanting valve may be composed of stainless steel, titanium, or an alloy.

A temperature monitoring mechanism such as a temperature strip may be coupled to the exterior wall of the sample holding unit. Additionally, a temperature altering device may be coupled to the exterior wall of the sample holding unit. The temperature altering device may be at least one heating coil or a heat exchanger The sampling apparatus may further include a three-way fitting with a first opening, a second opening and a third opening wherein the first opening of the three-way fitting is coupled to the second opening of the first check valve and the second opening of the three-way fitting is coupled to the trigger valve; and a pressure gauge wherein the pressure gauge is coupled to the third opening of the three-way fitting. A filter unit composed of a stainless steel mesh may be coupled to the second opening of the trigger valve wherein the filter unit filters fluid flowing through the trigger valve and the first check valve and into the sample holding unit.

The sampling apparatus may also include a bladder unit having a first opening wherein the bladder unit is held in the interior holding space of the sample holding unit and the first opening of the bladder unit is coupled to the first opening of the first check valve. Further, the sample holding unit may include a first opening, a second opening, a piston slidably mounted within the sample holding unit thereby creating a first chamber and a second chamber wherein a first chamber serves to receive a pressurized fluid through a first opening and the second chamber is adapted to receive a sample through the second opening.

According to another aspect of the invention, there is provided a sampling apparatus for collecting fluid samples from fluid environments comprising; a sample holding unit having an interior wall and an exterior wall creating an interior holding space, a first opening and a second opening wherein the first opening allows the interior holding space to be selectively in fluid communication with the exterior of the sample holding unit and operable to receive at least a portion of the fluid environment; a connector having a plurality of openings wherein a first opening of the plurality of openings is coupled to the first opening of the sample holding unit; a pressure relief device having a first opening and a second opening wherein the first opening is coupled to a second opening of the plurality of openings of the connector; a first flow regulating valve having a first opening, a second opening and an actuator wherein the first opening of the first flow regulating valve is coupled to the third opening of the plurality of openings of the connector; a second flow regulating valve having a first opening, a second opening and an actuator wherein the first opening of the ball valve is coupled to a second opening of the sample holding unit and the actuator is capable of regulating the flow of fluid from the fluid environment through the second flow regulating valve and into the sample holding unit; and a ball valve with a first opening, a second opening and an actuator wherein the first opening is coupled to the second flow the second opening of the second flow regulating valve and the actuator moves the ball valve from a closed position preventing fluid from passing into the sample holding unit to an open position allowing fluid to flow through the second opening of the ball valve and through the second flow regulating valve into the interior holding space of the sample holding unit.

According to another aspect of the invention, there is provided a fluid separation apparatus for separating a component from a composite fluid, the apparatus including a separation chamber having a first opening coupled to a sampling apparatus, a second opening in fluid communication with the fluid environment, a side wall around a vertical axis of the chamber, the side wall having a narrower diameter at the first opening wherein the second opening receives fluid from the fluid environment, the component of interest is separated from the fluid as the component of interest has a different specific gravity from the composite fluid, and the component of interest flows through the first opening passing into the sampling apparatus. The fluid separation apparatus may include at least one side port piercing the side wall around the vertical axis of the chamber in selective fluid communication with the fluid environment having a mechanism capable of being and closed. A pump may be coupled to the side port of the chamber wherein the pump pumps fluid from the exterior of the fluid separation apparatus to the interior of the fluid separation apparatus. A heating mechanism such as heating coils can be at least partially located within the interior of the chamber. Preferably, the power source for the heating mechanism located exterior to the chamber. The fluid separation may further include a clear tube with a first opening and a second opening wherein the first opening is coupled to the first opening of the chamber and the second opening is coupled to the sampling apparatus. An ultraviolet light mechanism may be positioned on the exterior of the side wall of the chamber wherein the ultraviolet light is directed at the chamber. Additionally, the fluid separation apparatus may include a funnel-shaped device having a first opening and a second opening wherein the first opening is substantially the same diameter as the second opening of the chamber and the first opening is coupled to the second opening of the chamber and the second opening is of a larger diameter than the second opening of the chamber and extends vertically away from the second opening of the chamber.

According to another aspect of the invention, there is provided a method of sampling fluid in a fluid environment, the method including lowering a sampling apparatus composed of a holding unit with at least one opening wherein the at least one opening of the holding unit is coupled to a first check valve and the first check valve is coupled to a trigger valve having an actuator coupled to a triggering mechanism; using the triggering mechanism to move the actuator of the trigger valve in a position to open the trigger valve and allow fluid to pass through the trigger valve and the first check valve into the holding unit; continuing to pass fluid through the trigger valve and the first check valve into the holding unit until the pressure of the interior of the holding unit reaches substantially the same pressure as the exterior of the interior of the holding unit wherein the first check valve seats, stopping the flow of fluid from the exterior of the holding unit from continuing to enter the holding unit; using the trigger mechanism to move the actuator of the trigger valve in a position to close the trigger valve and stop fluid from passing through the trigger valve; and raising the sampling apparatus to the surface of the fluid environment wherein the sampling apparatus contains a sample of fluid from the fluid environment.

According to yet another aspect of the invention, there is provided a method of sampling fluid in a fluid environment, the method including lowering a sampling apparatus composed of a holding unit with a first opening and a second opening; a connector having a plurality of openings wherein a first opening is coupled to the first opening of the holding unit; a pressure relief device coupled to a second opening of the connector; a first flow regulating valve having a first opening, a second opening and an actuator wherein the first opening of the first flow regulating valve is coupled to a third opening of the connector; a second flow regulating valve having a first opening, a second opening and an actuator wherein the first opening of the second flow regulating valve is coupled to the second opening of the holding unit; and a ball valve with a first opening, a second opening and an actuator wherein the first opening is coupled to the second opening of the second flow regulating valve; positioning the actuator of the ball valve in a position to open the ball valve and allow fluid to pass through the ball valve and the second flow regulating valve into the holding unit; continuing to pass fluid through the ball valve and the second flow regulating valve into the holding unit until the pressure of the interior of the holding unit reaches substantially the same pressure as the exterior of the interior of the holding unit wherein the second flow regulating valve is closed and then the ball valve is closed, stopping the flow of fluid from the exterior of the holding unit from continuing to enter the holding unit; positioning the actuator of the ball valve in a position to close the ball valve and preventing fluid from passing through the ball valve and the second flow regulating valve into the holding unit; and raising the sampling apparatus to the surface of the fluid environment wherein the sampling apparatus contains a sample of fluid from the fluid environment.

The method may further include connecting a fluid separation apparatus, as described herein, to the second opening of the ball valve of the sampling apparatus; allowing fluid to enter the fluid separation apparatus; separating a component to separate from the fluid; positioning the actuator of the ball valve in a position to allow the component to move from the fluid separation apparatus, through the ball valve and the second flow regulating valve and into the sample holding unit; positioning the actuator of the ball valve in a position to stop the movement of fluid from the separation apparatus, through the ball valve and the second flow regulating valve and into the sampling holding unit; and raising the sampling apparatus to the surface of the fluid environment wherein the sampling apparatus contains a sample of the component separated from the fluid from the fluid environment.

DETAILED DESCRIPTION OF EMBODIMENTS

The present apparatus and method are used to retrieve and store fluid samples from liquid environments. The components of the apparatus act in concert to remove a portion of the fluid found in the liquid environment, maintain the fluid samples at ambient conditions of the retrieval site in the sampling apparatus, and continue to maintain the fluid samples at ambient conditions of the retrieval site as the fluid samples are transferred from the sampling apparatus. Furthermore, the components of an embodiment act to separate a component of interest from the composite fluid of the liquid environment.

Figure 1:
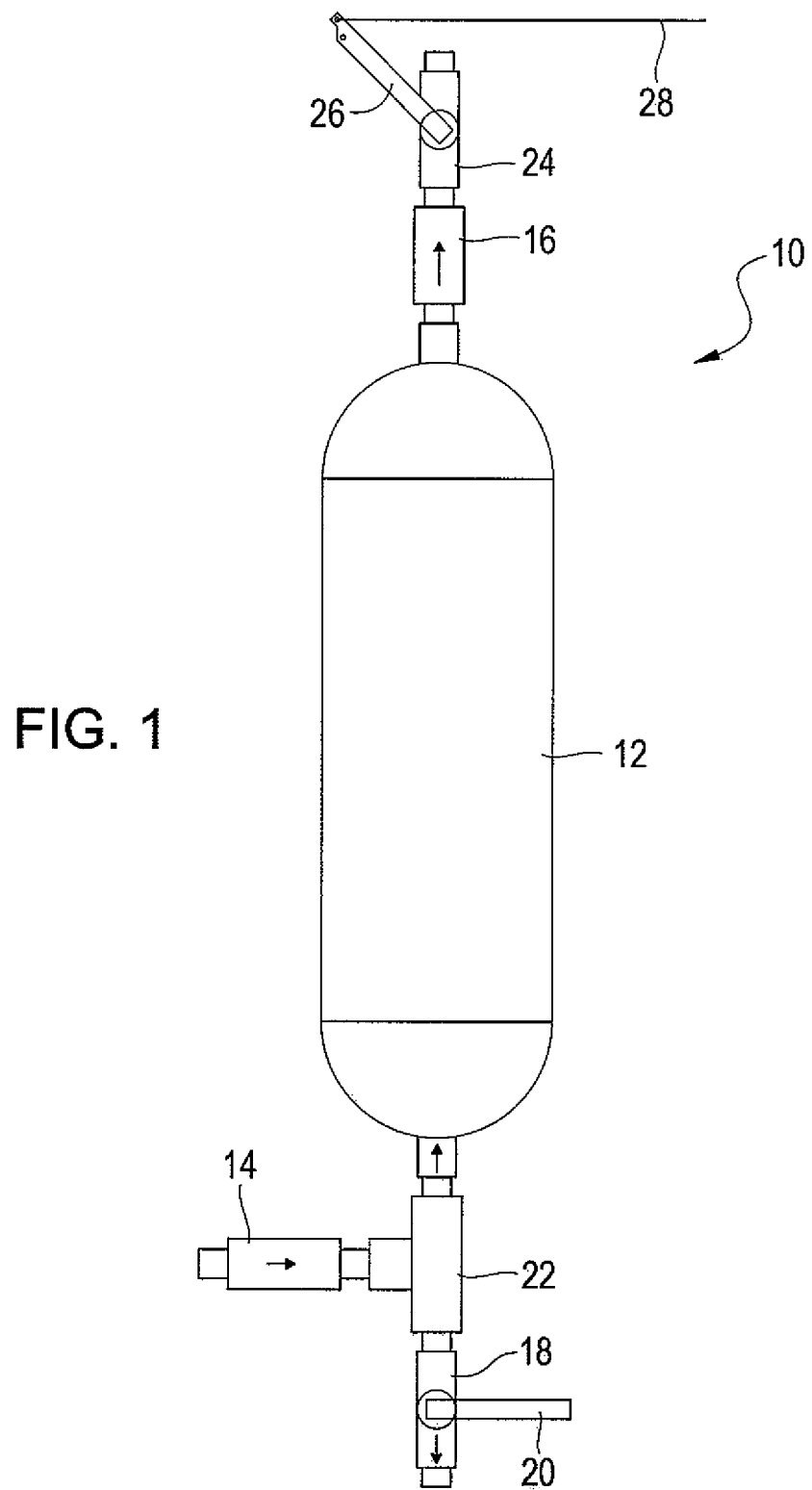
FIG. 1 is a perspective view of a sampling apparatus having an inlet check valve and an outlet check valve.

FIG. 1 depicts an overview of a sampling apparatus 10 used to retrieve at least one sample from a liquid environment. Sampling apparatus 10 includes a sample holding unit 12, an inlet check valve 14, an outlet check valve 16, a decanting valve 18 having an external actuator 20, a T-fitting 22, a trigger valve 24 having an external actuator 26, and a triggering mechanism 28 wherein the components of sampling apparatus 10 are coupled to allow selective fluid communication with the liquid environment external to the sampling apparatus 10. Materials for constructing the components of sampling apparatus 10 will be chosen for resistance to the liquid environment of interest.

Preparation of sampling apparatus 10 prior to deployment to the liquid environment requires that sample holding unit 12 be pressurized. A first end of the sample holding unit 12 is coupled to a first opening of outlet check valve 16 and a second opening of outlet check valve 16 is coupled to a first opening of trigger valve 24. A second end of sample holding unit 12 is coupled to a first opening of T-fitting 22. A second opening of T-fitting 22 is coupled to first opening of inlet check valve 14 and a third opening of T-fitting 22 is coupled to a first opening of decanting valve 18.

To pressurize sample holding unit 12, actuator 20 of decanting valve 18 is positioned to open decanting valve 18 while actuator 26 of trigger valve 24 is positioned to close trigger valve 24. One end of a tube is coupled to decanting valve 18 and a second end of the tube is coupled to a gas pumping apparatus. Gas pumping apparatus is powered and turned on, pressurizing sample holding unit 12 to the appropriate pressure, which is determined by the depth and location of the liquid environment of interest. Once sample holding unit 12 reaches the appropriate pressure, actuator 20 of decanting valve 18 is positioned to close decanting valve 18, stopping the flow of gas into sampling apparatus. Tube is removed from decanting valve 18. Triggering mechanism 28 is then coupled to trigger valve 26.

Sampling apparatus 10 is then deployed to the depth and location of the liquid environment of interest by a deployment method. The deployment method can be a drop line from a ship, a sample carousel 30 where a plurality of sampling apparatuses can be deployed or a Remotely Operated Vehicle ("ROV"). In this embodiment as referred in FIG. 6, the deployment method associated with sampling is sample carousel 30 where a plurality of sampling apparatuses can be attached to a support frame 32 extending vertically and away from a base platform 34. The plurality of sampling apparatuses is coupled to support frame 32 by any conventional attachment means 36. Each of the plurality of sampling apparatuses are coupled to a separate triggering mechanism allowing each of the plurality of sampling apparatuses to collect fluid from different sites in a liquid environment.

To obtain a fluid sample from the liquid environment, triggering mechanism 28 is activated where triggering mechanism 28 positions actuator 26 of trigger valve 24 to the open position. The gas stored in sampling holding unit 12 exits sampling apparatus 10 through trigger valve 24 causing the internal pressure of sampling apparatus 10 to decrease, leading to a pressure differential between the interior of sample holding unit 12 and the exterior of sample holding unit 12. Once the pressure differential reaches a specific point, the inlet check valve 14 opens, allowing fluid to flow through inlet check valve 14, T-fitting 22, and into sample holding unit 12. As the fluid flows into sample holding unit 12, replacing the gas, the pressure differential will begin to decrease, moving toward equilibrium. Once the internal pressure of sample holding unit 12 reaches a point substantially similar to the external pressure of the liquid environment, inlet check valve 14 will close. Triggering mechanism 28 is activated a second time to close trigger valve 24 preventing loss of fluid from sample holding unit. Fluid in sample holding unit 12 can then be retrieved. As fluid in sample holding unit 12 is retrieved, it remains at substantially equivalent pressure as the retrieval site.

Figure 2:
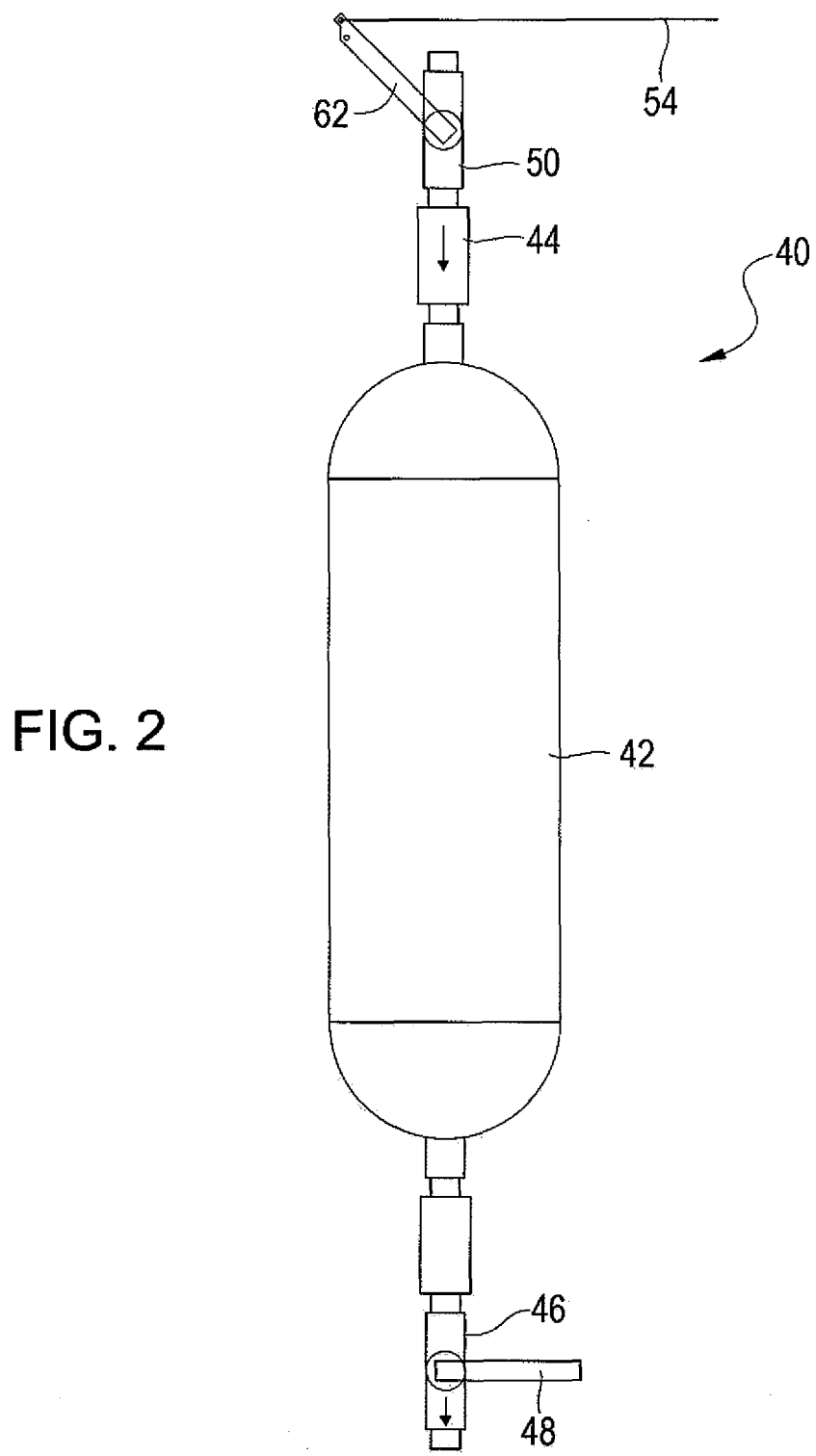
FIG. 2 is a perspective view of a sampling apparatus having a check valve that performs as an inlet and an outlet.

FIG. 2 depicts an overview of a sampling apparatus 40 used to retrieve at least one sample from a liquid environment. Sampling apparatus 40 includes a sample holding unit 42, a check valve 44, a decanting valve 46 having an external actuator 48, a trigger valve 50 having an external actuator 52, and a triggering mechanism 54 wherein the components of sampling apparatus 40 are coupled to allow selective fluid communication between the interior of sampling apparatus and the liquid environment external to sampling apparatus 40. Materials for constructing the components of sampling apparatus 40 will be chosen for resistance to the liquid environment of interest.

Preparation of sampling apparatus 40 prior to deployment to the liquid environment can include either sampling apparatus 40 at atmospheric pressure or at negative pressure. Sampling apparatus 40 from FIG. 2 has a first end of sample holding unit 42 coupled to a first opening of check valve 44 which is coupled to a first opening of trigger valve 50. A second end of sample holding unit 40 is coupled to a first opening of decanting valve 46.

If sampling apparatus 40 is to be deployed with its internal pressure at atmospheric pressure, sampling apparatus 40 is flushed with gas to evacuate any possible contaminants located in the interior of sampling apparatus 40. Sampling apparatus 40 is coupled to a gas pumping apparatus at trigger valve 50 wherein trigger valve 50 and decanting valve 46 are open to gas flow. The gas pumping apparatus pumps gas through trigger valve 50 and exits decanting valve 46 for a specified period of time. Once sampling apparatus 40 has been flushed with gas, the gas pumping apparatus is powered off and sampling apparatus 40 is allowed to reach atmospheric pressure. Trigger valve 50 and decanting valve 46 are closed to prevent gas or fluids from entering sampling apparatus 40.

If sampling apparatus 40 is to be deployed at negative pressure, a vacuum pump is to create a vacuum in sampling apparatus 40. Trigger valve 50 is closed and decanting valve 46 is opened. The vacuum pump is coupled to decanting valve 46 and, once powered on, creates a vacuum in sampling apparatus 40 to the desired pressure level. Once the desired pressure level is reached, decanting valve 46 is closed, vacuum pump is shut down, and vacuum pump is uncoupled from decanting valve 46.

Figure 6:
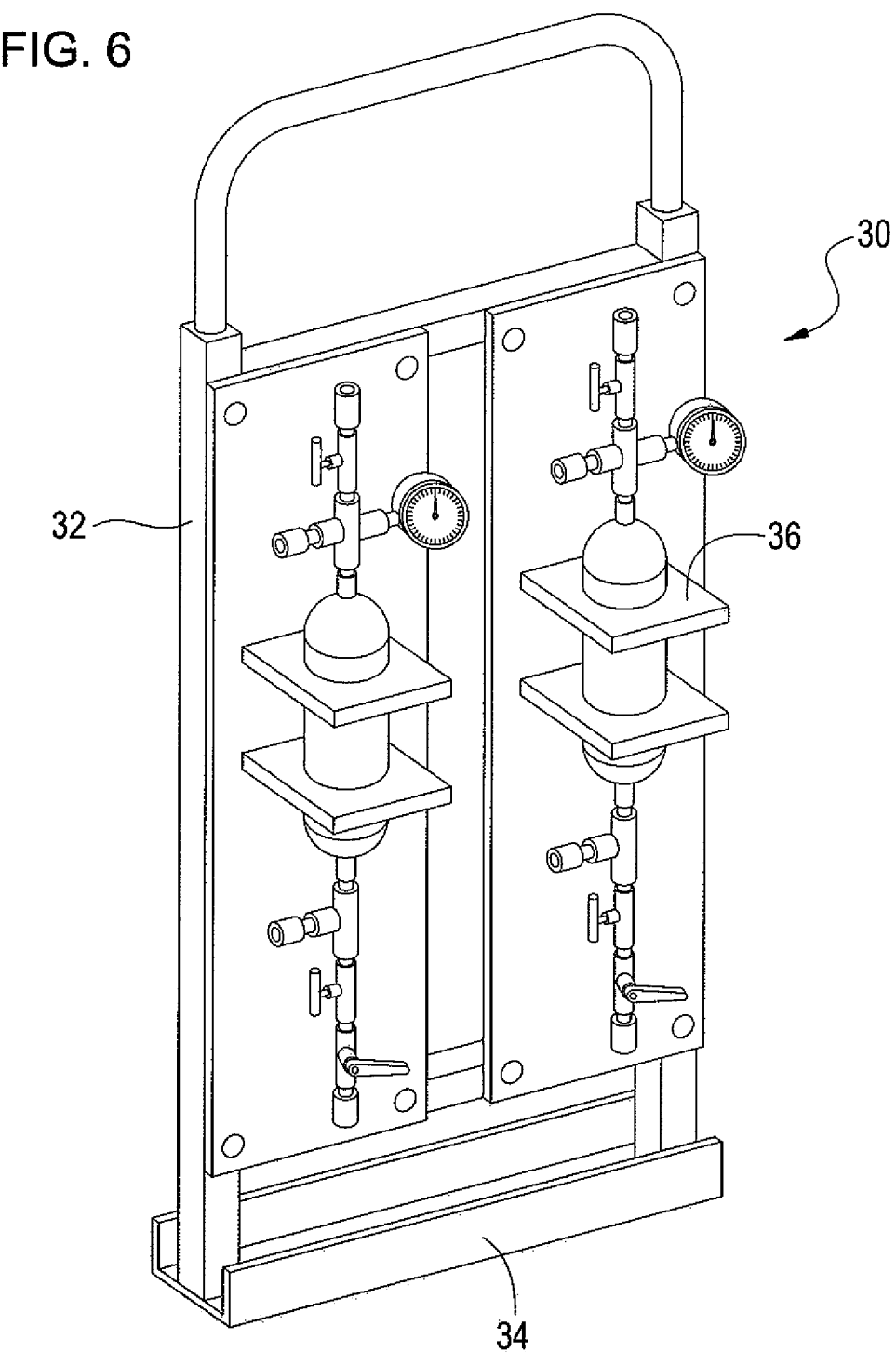
FIG. 6 is a perspective view of two sampling apparatuses of FIG. 3 coupled to a sample carousel.

Sampling apparatus 46 is then deployed to the depth and location of the liquid environment of interest by a deployment method. The deployment method can be a drop line from a ship, a sample carousel 30 where a plurality of sampling apparatuses can be deployed or a Remotely Operated Vehicle ("ROV"). In this embodiment, as depicted in FIG. 6, the deployment method depicted uses sample carousel 30 described herein.

To obtain a fluid sample from the liquid environment, once sampling apparatus 40 reaches the desired location, triggering mechanism 54 is activated whereby triggering mechanism 54 positions actuator 52 of trigger valve 50 to the open position. Fluid flows through trigger valve 50 and check valve 44 into sample holding unit 44. As the fluid flows into sample holding unit 42, the internal pressure of sampling apparatus 40 will begin to approach the pressure of the external liquid environment. Once the internal pressure of sample holding unit 42 reaches a point substantially similar to the external pressure of the liquid environment, check valve 44 will close. Triggering mechanism 54 is activated a second time to close trigger valve 50 preventing loss of fluid from sample holding unit 42. Fluid in sample holding unit 42 can then be retrieved. As fluid in sample holding unit 42 is retrieved, it remains at substantially similar pressure as the retrieval site.

Once sampling apparatus from FIGS. 1 and 2 are retrieved, fluid from sample holding unit 12, 42 can be stored or removed and analyzed. Removal of fluid from sample holding unit 12, 42 can be accomplished using a number of transfer mechanisms that maintain the physical and chemical characteristics of the fluid for accurate analysis to be completed on the fluid. The transfer mechanism is coupled to decanting valve 18, 46 of sampling apparatus 10, 40 allowing the fluid to exit sampling apparatus 10, 40 by flowing from sample holding unit 12, 42 through decanting valve 18, 46 and into transfer method.

Figure 3:
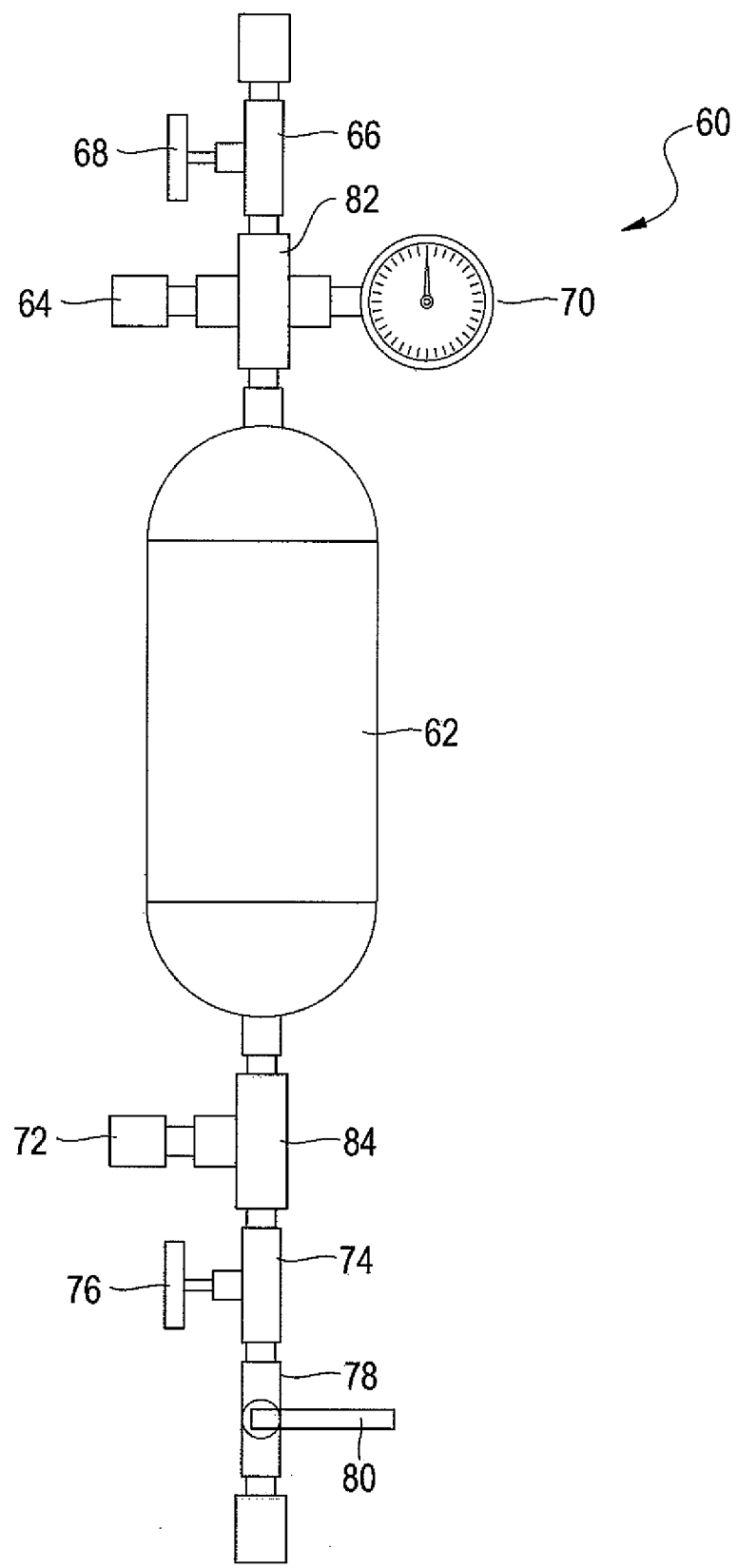
FIG. 3 is a perspective view of sampling apparatus having a first rupture disc, a second rupture disc, a first flow regulating valve, a second flow regulating valve, and a ball valve with an actuator.

Referring to FIG. 3, a sampling apparatus 60 is depicted capable of retrieving, storing and transporting a fluid obtained from a liquid environment. Sampling apparatus 60 includes a sample holding unit 62 for holding of fluid, a first pressure relief device 64, a first flow regulating valve 66 with an external actuator 68, a pressure monitoring device 70, a second pressure relief device 72, a second flow regulating valve 74 with an external actuator 76 used to selectively permit, control the rate and prevent flow through to sample holding unit 62, and a ball valve 78 with an external actuator 80 used to selectively permit and prevent flow through to sample holding unit 62. The components of sampling apparatus 60 allow portions of fluid to be collected from liquid environments external to sampling apparatus 60.

Sampling apparatus 60 is deployed at atmospheric pressure and is flushed with gas to evacuate any possible contaminants located in the interior of sampling apparatus 60. Sampling apparatus 60 is coupled to a gas pumping apparatus at a second opening of first flow regulating valve 66. A second opening of first flow regulating valve 66 is coupled to a first opening of a four-way connector 82. First pressure relief device 64 is coupled to a second opening of four-way connector 82 while a pressure monitoring device 70 is coupled to a third opening of four-way connector 82. Sample holding unit 62 is coupled at its first end to a fourth opening of four-way connector 82 and at its second end to a first opening of a three-way connector 84. A second opening of three-way connector 84 is coupled to a second pressure relief device 72 and a third opening of three-way connector 84 is coupled to a first end of second flow regulating valve 74. A second end of second flow regulating valve 74 is coupled to a first end of a ball valve 78.

To allow gas to flow through sampling apparatus 60, first 66 and second flow regulating valves 74 and ball valve 78 are opened to allow gas flow through sampling apparatus 60. The gas pumping apparatus pumps gas through first flow regulating valve 66 and exits at ball valve 78. Once sampling apparatus 60 has been flushed with gas, the gas pumping apparatus is powered off and sampling apparatus 60 is allowed to reach atmospheric pressure. First 66 and second flow regulating valves 74 and ball valve 78 are closed to prevent gas or fluids to enter sampling apparatus 60.

To obtain a fluid sample from a specific point within the liquid environment, once sampling apparatus 60 reaches the desired location, second flow regulating valve 74 and ball valve 78 are opened. First flow regulating valve 66 is opened to allow fluid to move into sampling apparatus 60 through ball 78 and second flow regulating valves 74. Fluid flows through ball 78 and second flow regulating valve 74 into sample holding unit 62. As the fluid flows into the sample holding unit 62, the internal pressure of sampling apparatus 60 approaches the pressure of the external liquid environment, reflected by pressure monitoring device 70. Once the internal pressure of the sample holding unit 62 reaches a point substantially similar to the external pressure of the liquid environment, first 66 and second flow regulating valves 74 and ball valve 78 are closed. Fluid in sample apparatus 60 can then be retrieved. As fluid in sample apparatus 60 is retrieved, the fluid remains at substantially equivalent pressure as that of the retrieval site.

Referring to FIGS. 1, 2 and 3, sampling apparatuses 10, 40, 60 can be adapted based on the environmental conditions of the retrieval site. For example, a filter can be included in the construction of sample apparatuses 10, 40, 60 at the point of fluid entry into the interior of sampling apparatuses 10, 40, 60. Filters can function to prevent solid particles of specific size from entering sampling apparatuses 10, 40, 60. To prevent solid particles of specific size from entering sampling apparatuses 10, 40, 60, steel mesh or polyvinyl filters of differing pore sizes can be utilized, preferably coupled to inlet check valve 14 of FIG. 1, check valve 44 of FIG. 2, and second opening of ball valve 78 of FIG. 3. Alternatively, membranes can be chosen which function to exclude certain gases from entering sampling apparatuses 10, 40, 60. To concentrate or exclude specific gases, inorganic or organic membranes can be utilized, including but not limited to nanoparticle membranes, polymer-based membranes, and certain inorganic membranes composed of such materials as ceramic, palladium alloy or zeolite.

Once sampling apparatuses 10, 40, 60 from FIGS. 1, 2 and 3 are retrieved from the liquid environment, fluid stored in sample holding unit 12, 42, 62 can be kept in storage for later analysis or the fluid can be removed and immediately analyzed. Removal of fluid from sample holding unit 12, 42, 62 can be accomplished using a number of transfer mechanisms that maintain the physical and chemical characteristics of the fluid for accurate analysis to be completed on the fluid. For removal of fluid from sampling apparatuses 10, 40 in FIGS. 1 and 2, the transfer mechanism is coupled to decanting valve 18, 46 of sampling apparatus 10, 40 allowing the fluid to exit sampling apparatus 10, 40 by flowing from sample holding unit 12, 42 through decanting valve 18, 46 and into transfer method. For removal of fluid from sampling apparatus 60 in FIG. 3, the transfer mechanism is coupled to ball valve 78, where ball valve 78 and second flow regulating valve 74 are opened allowing the fluid to exit sampling apparatus 60 by flowing from sample holding unit 62 through second flow regulating valve 74 and ball valve 78 and into transfer method. Referring to FIG. 3, sampling apparatus 60 can also include a port for direct withdrawal of gases from sampling apparatus 60.

Materials for constructing the components of sampling apparatus 10, 40, 60 can be chosen based on the needs presented by the liquid environment of interest. For high hydrostatic pressure sites, such as deep sea fluid retrieval, materials can be chosen based on ratings by the United States Department of Transportation, such as 316 stainless steel combined with Teflon seals. Materials used for high pressure environments must be chosen to not only withstand the ambient hydrostatic pressure of the depth of interest, but also the increase in pressure exerted by the fluid as the sample apparatus 10, 40, 60 is exposed to increasing temperatures as sampling apparatus 10, 40, 60 is retrieved. For corrosive environments, titanium or titanium alloys can be chosen.

Other additions to the embodiments described herein include coupling a temperature altering device, such as a heat exchanger, to either the exterior or interior of sampling apparatuses 10, 40, 60 to maintain the temperature of the fluid collected at the substantially equivalent ambient temperature of the retrieval site.

For retrieving of a component of interest from a liquid environment, a separation apparatus 90 can be coupled to a sampling apparatus 60. More particularly referring to FIG. 4, separation apparatus 90 is composed of a separation chamber 92 having a first end 94, a sidewall 96 surrounding the vertical axis of separation chamber and a second end 98. The diameter of first end 94 of separation chamber 92 is of a size to easily couple separation chamber 92 to sampling apparatus 60 by coupling first end 94 of separation chamber 92 to a first end of a two-way connector 100 and second end of ball valve 78 to a second end of two-way connector 100 where separation chamber 92 extends vertically away from and below sampling apparatus 60.

Separation apparatus 90 can be used to concentrate gases from a composite fluid of a liquid environment. Separation apparatus 90 coupled to sampling apparatus 60 is deployed to a location of interest of the liquid environment wherein separation apparatus 90 coupled to sampling apparatus 60 is oriented so that the vertical axis of separation chamber 92 is perpendicular to a bottom surface of the liquid environment. The composite fluid of the liquid environment flows into separation chamber 92. Based on buoyancy differences, gases rise through the fluid column, coming out of solution. The gas bubbles rise toward first end 94 of separation chamber 92, becoming numerous enough to displace the remaining composite fluid, creating a gas phase adjacent to and below first end 94 of separation chamber 92. The gas phase located in separation chamber 92 can be collected by sampling apparatus 60 by opening second flow regulating valve 74 and ball valve 78, allowing the gas phase to flow from separation apparatus 90 through second flow regulating valve 74 and ball valve 78 and into sample holding unit 62. Second flow regulating valve 74 and ball valve 78 are then closed, trapping the gas phase inside sample holding unit 62. This procedure for gas retrieval can be repeated until the amount of the gas phase inside sample holding unit 62 reaches an acceptable level.

If the liquid environment of interest is at a temperature in which gas hydrates form, a heat source 106 can be coupled to the interior of separation chamber 92. A power source for the heat source 106 can be provided as a battery pack coupled to heat source 106 or, if separation apparatus 90 coupled to sampling apparatus 60 was deployed using an ROV, the ROV can provide the power supply to heat source 106. The heat source 106 can be a plurality of heating coils or heating elements in any form to provide a heat source.

Hydrocarbons, such as oil, are another component of interest found in liquid environments. To separate oil from a composite fluid, separation apparatus 90 coupled to sampling apparatus 60 is deployed to a location of interest of the liquid environment wherein separation apparatus 90 coupled to sampling apparatus 60 is oriented perpendicular to a bottom surface of the liquid environment.

Once separation apparatus 90 coupled to sampling apparatus 60 is deployed in a site of interest, the composite fluid of the liquid environment flows into separation chamber 92. As hydrocarbons, such as oil, and water are immiscible, oil particles separate from the composite fluid and rise vertically through the fluid column away from the bottom of the liquid environment. The oil particles rise toward first end 94 of separation chamber 92, becoming numerous enough to displace the remaining composite fluid, creating an oil phase adjacent to and below first end of separation chamber 92. The oil phase located in the interior of separation chamber 92 can be collected by sampling apparatus 60 by opening second flow regulating valve 74 and ball valve 78, allowing the oil phase to flow from separation apparatus 90 through second flow regulating valve 74 and ball valve 78 and into sample holding unit 62. Second flow regulating valve 74 and ball valve 78 are then closed, trapping the oil phase inside sample holding unit 62. This procedure for oil retrieval can be repeated until the amount of the oil inside sample holding unit 62 reaches an acceptable level.

Hydrocarbons, such as oil, may be at low concentrations in a composite fluid. To increase the concentration of oil particles, separation chamber 92 can include a side port 102 intersecting sidewall 96 of separation chamber 92. Side port 102 is coupled to a relief tube and a closure device 104, allowing selective fluid communication between separation chamber 92 by way of side port 102. Once the oil separates from the initial composite fluid, the relief tube and closure device 104 can be opened, allowing pulsing of fresh composite fluid into separation chamber 92. This pulsing is repeated until a sufficient amount of oil has been collected in sample holding unit 62. A pump can be included on one end of relief tube to facilitate pulsing.

To clearly monitor the oil and water separation, separation apparatus 90 can include a light source, such as ultraviolet, where the light source is directed toward separation chamber. A power supply to the light source can be provided as a battery pack coupled to the light source or, if separation apparatus 90 coupled to sampling apparatus 60 were deployed using an ROV, the ROV can provide the power supply to the light source. Further adaptations to separation apparatus 90 can include a clear sight tube where clear sight tube is located between separation chamber 90 and connector coupled to sampling apparatus 60. Clear sight tube allows monitoring of the aggregation of gas or hydrocarbons. For ease of placement of separation apparatus 90, a large funnel-shaped device can be coupled to second end 98 of separation chamber 92.

Figure 4:
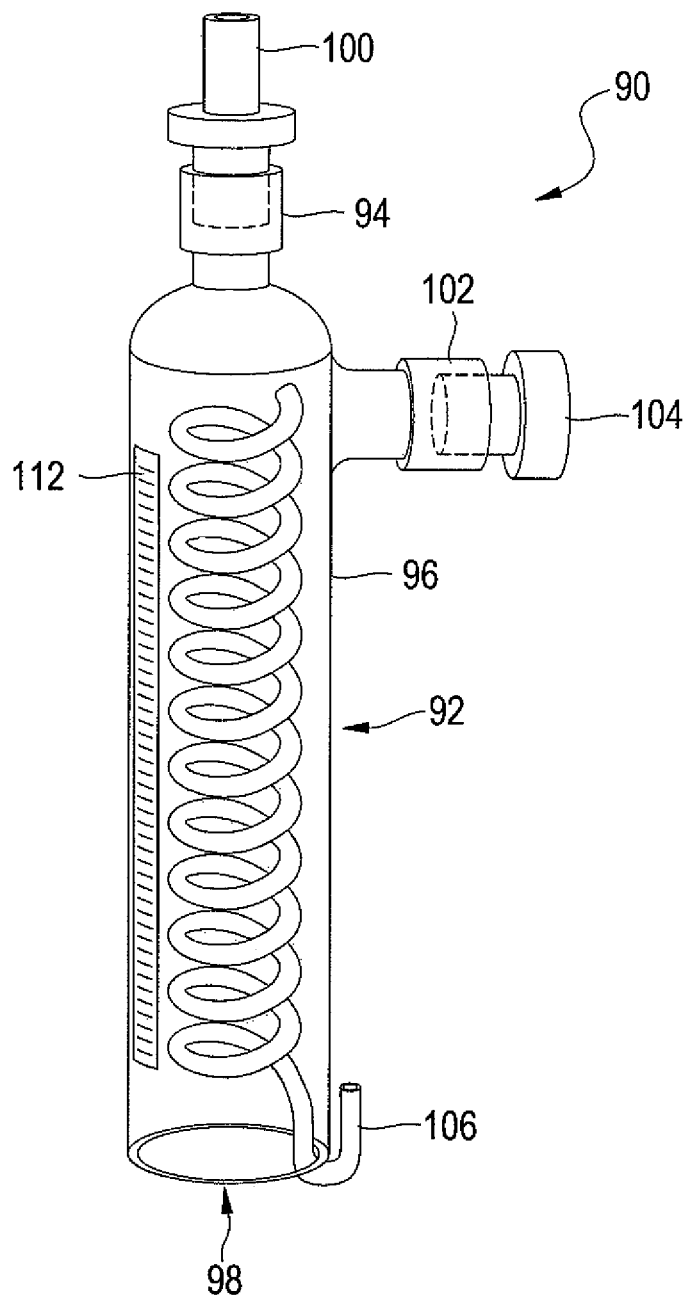
FIG. 4 is a perspective view of a separation apparatus.

Multiple adaptations can be made to the aforementioned sampling apparatuses and separation apparatus, depicted in FIGS. 1, 2, 3, and 4. Temperature monitoring devices can be placed on the exterior or interior of any of the apparatuses from FIGS. 1, 2, 3, and 4. Referring specifically to FIG. 4, separation chamber 92 can include a temperature strip 112 for monitoring temperature.

Figure 5:
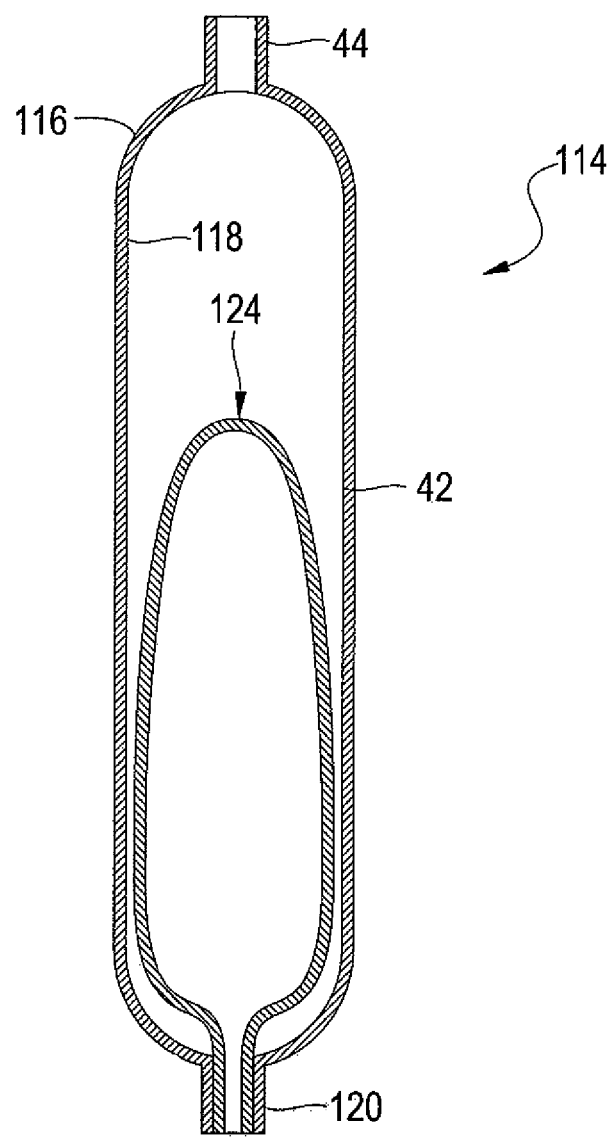
FIG. 5 is an interior view of a constant pressure sample holding unit.

Although sample holding unit 12, 42, 62 of the aforementioned sampling apparatuses 10, 40, 60 is illustrated as a cylinder, the shape and interior volume of sample holding unit 12, 42, 62 can vary based on the needs and characteristics of the liquid environment. Sample holding unit 12, 42, 62 can be a holding unit having an exterior surface, an interior surface and at least one opening. Alternatively, sample holding unit can be a constant pressure holding unit 114, an example of which is depicted in FIG. 5. Constant pressure holding unit 114 has an exterior surface 116, an interior surface 118 and a first opening 120 and a second opening 122. Within interior surface 118 of constant pressure holding unit 114, a bladder 124 is coupled to first opening 120 wherein bladder 124 acts as the fluid holding area. As portions of the fluid are withdrawn from bladder 124 for analysis, maintenance of pressure substantially equivalent to the retrieval site is achieved by coupling second opening 122 of constant pressure containment unit 114 to a gas pumping mechanism and a pressure gauge where gas is pumped into constant pressure holding unit 114 as fluid is withdrawn.

Alternatively, a constant pressure holding unit can also be used in which the unit has an exterior surface, an interior surface and a piston movably mounted in the interior of the constant pressure holding unit where the piston separates the internal space of the constant pressure holding unit into two chambers. One chamber provides space for fluid to be introduced and stored in the constant pressure holding unit and the second chamber is filled with gas to maintain a constant pressure in the constant pressure holding unit, an apparatus of which is described in U.S. Pat. No. 4,922,764, which is incorporated by reference herein in its entirety.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed:

1. A sampling apparatus for collecting fluid samples from fluid environments comprising:
   a sample holding unit having an interior wall and an exterior wall creating an interior holding space, a first opening and a second opening, the first opening and the second opening being fluidly coupled via the interior holding space and configured for allowing the interior holding space to be selectively in fluid communication with the exterior of the sample holding unit;
   a first check valve having a first end coupled to the first opening of the sample holding unit wherein the check valve is configured to open in response to a pressure differential between the interior holding space of the sample holding unit and the exterior of the sample holding unit;
   a trigger valve having an actuator wherein the trigger valve is coupled to a second end of the check valve and the actuator is configured to move the trigger valve from a closed position preventing fluid from passing into the sample holding unit to an open position allowing fluid to flow into the interior holding space of the sample holding unit, the first check valve being coupled between the sample holding unit and the trigger valve;
   a triggering mechanism coupled to the actuator of the trigger valve wherein the trigger mechanism is configured to operate the actuator of the trigger valve; and
   a decanting valve having a first end and an actuator wherein the first end of the decanting valve is coupled to the second opening of the sample holding unit, wherein the actuator is configured to move the decanting valve from a closed position preventing fluid in the interior holding space of the sample holding unit to flow out of the sample holding unit to an open position allowing fluid to flow from the sample holding unit through the decanting valve to the exterior of the sample holding unit.

2. The sampling apparatus of claim 1 further comprising a second check valve coupled to and between the second opening of the sample holding unit and the decanting valve.

3. The sampling apparatus of claim 2 wherein the sampling holding unit, the first check valve, the trigger valve, the second check valve and the decanting valve are composed of a material selected from the group consisting of stainless steel, titanium and an alloy.

4. The sampling apparatus of claim 2 wherein the first opening and the second opening of the sample holding unit extend through opposite ends of the sampling holding unit.

5. The sampling apparatus of claim 1 wherein the first check valve and the trigger valve are arranged along a longitudinal axis of the sampling holding unit.

6. A sampling apparatus for collecting fluid samples from fluid environments comprising:
   a sample holding unit having an interior wall and an exterior wall creating an interior holding space, at least one opening allowing the interior holding space to be selectively in fluid communication with the exterior of the sample holding unit and operable to receive at least a portion of the fluid environment;
   a first check valve having a first end coupled to a first opening of the at least one opening of the sample holding unit wherein the check valve opens in response to a pressure differential between the interior holding space of the sample holding unit and the exterior of the sample holding unit;
   a trigger valve having a first opening, a second opening and an actuator wherein the first opening of the trigger valve is coupled to a second opening of the check valve and the actuator moves the trigger valve from a closed position preventing fluid from passing into the sample holding unit to an open position allowing fluid to flow through the trigger valve and the first check valve into the interior holding space of the sample holding unit;
   a triggering mechanism coupled to the actuator of the trigger valve wherein trigger mechanism operates the actuator of the trigger valve; and
   a temperature monitoring mechanism coupled to the exterior wall of the sample holding unit.

7. The sampling apparatus of claim 6 wherein the temperature monitoring mechanism is a temperature strip coupled to the exterior wall of the sample holding unit.

8. The sampling apparatus of claim 2 further comprising a three-way fitting coupled to and between the sample holding unit and the decanting valve.

9. A sampling apparatus for collecting fluid samples from fluid environments comprising:
   a sample holding unit having an interior wall and an exterior wall creating an interior holding space, at least one opening allowing the interior holding space to be selectively in fluid communication with the exterior of the sample holding unit and operable to receive at least a portion of the fluid environment;
   a first check valve having a first end coupled to a first opening of the at least one opening of the sample holding unit wherein the check valve opens in response to a pressure differential between the interior holding space of the sample holding unit and the exterior of the sample holding unit;
   a trigger valve having a first opening, a second opening and an actuator wherein the first opening of the trigger valve is coupled to a second opening of the check valve and the actuator moves the trigger valve from a closed position preventing fluid from passing into the sample holding unit to an open position allowing fluid to flow through the trigger valve and the first check valve into the interior holding space of the sample holding unit;

a triggering mechanism coupled to the actuator of the trigger valve wherein trigger mechanism operates the actuator of the trigger valve, and a temperature altering device coupled to the exterior wall of the sample holding unit.

10. The sampling apparatus of claim 9 wherein the temperature altering device is a at least one heating coil.

11. The sampling apparatus of claim 9 wherein the temperature altering device is a heat exchanger.

12. The sampling apparatus of claim 1 further comprising a filter unit coupled to the trigger valve wherein the filter unit filters fluid flowing through the trigger valve and the first check valve and into the sample holding unit.

13. The sampling apparatus of claim 12 wherein filter unit is composed of a stainless steel mesh.

14. A sampling apparatus for collecting fluid samples from fluid environments comprising:

a sample holding unit having an interior wall and an exterior wall creating an interior holding space, at least one opening allowing the interior holding space to be selectively in fluid communication with the exterior of the sample holding unit and operable to receive at least a portion of the fluid environment;

a first check valve having a first end coupled to a first opening of the at least one opening of the sample holding unit wherein the check valve opens in response to a pressure differential between the interior holding space of the sample holding unit and the exterior of the sample holding unit;

a trigger valve having a first opening, a second opening and an actuator wherein the first opening of the trigger valve is coupled to a second opening of the check valve and the actuator moves the trigger valve from a closed position preventing fluid from passing into the sample holding unit to an open position allowing fluid to flow through the trigger valve and the first check valve into the interior holding space of the sample holding unit;

a triggering mechanism coupled to the actuator of the trigger valve wherein trigger mechanism operates the actuator of the trigger valve; and a bladder unit having a first opening wherein the bladder unit is held in the interior holding space of the sample holding unit and the first opening of the bladder unit is coupled to the first opening of the first check valve.

15. A sampling apparatus for collecting fluid samples from fluid environments comprising:

a sample holding unit having an interior wall and an exterior wall creating an interior holding space, at least one opening allowing the interior holding space to be selectively in fluid communication with the exterior of the sample holding unit and operable to receive at least a portion of the fluid environment;

a first check valve having a first end coupled to a first opening of the at least one opening of the sample holding unit wherein the check valve opens in response to a pressure differential between the interior holding space of the sample holding unit and the exterior of the sample holding unit;

a trigger valve having a first opening, a second opening and an actuator wherein the first opening of the trigger valve is coupled to a second opening of the check valve and the actuator moves the trigger valve from a closed position preventing fluid from passing into the sample holding unit to an open position allowing fluid to flow through the trigger valve and the first check valve into the interior holding space of the sample holding unit;

a triggering mechanism coupled to the actuator of the trigger valve wherein trigger mechanism operates the actuator of the trigger valve;

wherein the sample holding unit has a first opening, a second opening, a piston slidably mounted within the sample holding unit thereby creating a first chamber and a second chamber wherein a first chamber serves to receive a pressurized fluid through a first opening and the second chamber is adapted to receive a sample through the second opening.

16. A sampling apparatus for collecting fluid samples from fluid environments comprising:

a sample holding unit having an interior wall and an exterior wall creating an interior holding space, a first opening and a second opening wherein the first opening allows the interior holding space to be selectively in fluid communication with the exterior of the sample holding unit and operable to receive at least a portion of the fluid environment;

a connector having a plurality of openings wherein a first opening of the plurality of openings is coupled to the first opening of the sample holding unit;

a pressure relief device having a first opening and a second opening wherein the first opening is coupled to a second opening of the plurality of openings of the connector;

a first flow regulating valve having a first opening, a second opening and an actuator wherein the first opening of the first flow regulating valve is coupled to the third opening of the plurality of openings of the connector;

a second flow regulating valve having a first opening, a second opening and an actuator wherein the first opening of the second flow regulating valve is coupled to a second opening of the holding unit and the actuator is capable of regulating the flow of fluid from the fluid environment through the second flow regulating valve and into the holding unit;

a ball valve with a first opening, a second opening and an actuator wherein the first opening is coupled to the second opening of the second flow regulating valve and the actuator moves the ball valve from a closed position preventing fluid from passing into the sample holding unit to an open position allowing fluid to flow through the second opening of the ball valve and through the second flow regulating valve into the interior holding space of the sample holding unit, and a temperature monitoring mechanism coupled to the exterior wall of the sample holding unit.

17. A sampling apparatus for collecting fluid samples from fluid environments comprising:

a sample holding unit having a first end with a first opening, a second end with a second opening and a chamber, the first opening and the second opening being fluidly coupled via the chamber, a first valve assembly connected to the first end and fluidly coupled to the first opening, and a second valve assembly connected to the second end and fluidly coupled to the second opening, wherein the first valve assembly includes a first pressure release device, a first flow regulating valve and a ball valve, the first pressure release device being coupled to and between the first opening and the first flow regulating valve and the first flow regulating valve being coupled to and between the first pressure relief device and the ball valve, and wherein the second valve assembly includes a second pressure release device and a second flow regulating valve, the pressure relief device being coupled to and between the second opening and the second flow regulating valve.

18. The sampling apparatus of claim 17 wherein the second valve assembly includes a pressure gauge coupled to and between the second opening and the second flow regulating valve.

19. The sampling apparatus of claim 17 wherein the second valve assembly includes a removable cap configured for opening and closing fluid access into and out of the second valve assembly.

20. The sampling apparatus of claim 17 wherein the first valve assembly and the second valve assembly extend along a longitudinal axis of the sample holding unit.

\* \* \* \* \*